US008404454B2

(12) United States Patent
Smith

(10) Patent No.: US 8,404,454 B2
(45) Date of Patent: Mar. 26, 2013

(54) METHOD FOR IDENTIFYING A T-CELL RECEPTOR PROTECTIVE AGAINST A DISEASE

(75) Inventor: Adrian Smith, Oxford (GB)

(73) Assignee: Isis Innovation Limited, Oxford (GB)

( * ) Notice: Subject to any disclaimer, the term of this patent is extended or adjusted under 35 U.S.C. 154(b) by 219 days.

(21) Appl. No.: 12/745,862

(22) PCT Filed: Dec. 3, 2007

(86) PCT No.: PCT/GB2007/004635
§ 371 (c)(1),
(2), (4) Date: Jul. 21, 2010

(87) PCT Pub. No.: WO2009/071864
PCT Pub. Date: Jun. 11, 2009

(65) Prior Publication Data
US 2010/0279317 A1  Nov. 4, 2010

(51) Int. Cl.
*G01N 33/53* (2006.01)
(52) U.S. Cl. .................................... 435/7.21
(58) Field of Classification Search .................. None
See application file for complete search history.

(56) References Cited

U.S. PATENT DOCUMENTS

| 5,989,565 | A | 11/1999 | Storkus et al. | |
|---|---|---|---|---|
| 2003/0103946 | A1* | 6/2003 | Stauss et al. | 424/93.21 |
| 2005/0114910 | A1* | 5/2005 | Lone et al. | 800/3 |

FOREIGN PATENT DOCUMENTS
EP  1 118 860  7/2001

OTHER PUBLICATIONS

Hoft et al., Infect Immun. Jan. 2000;68(1):197-204.*
Duthie et al., Clin. Vaccine Immunol. 2007, 14(8):1005.*
Koelle, Methods. Mar. 2003;29(3):213-26.*
Cohen et al., Cancer Res 2006;66:8878-8886.*
Schumacher, Nat Rev Immunol. Jul. 2002;2(7):512-9.*
Zhao et al., J Immunother 2006;29:398-406.*
Webster's New World Dictionary, Third College Edition, 1988, pp. 1067-1068.*
Attuil et al., Comparative T cell receptor repertoire selection by antigen after adoptive transfer: A glimpse at an antigen-specific preimmune repertoire. *Proc. Natl. Acad. Sci. USA*, 97(15): 8473-8 (2000).
Barry et al., Expression library immunization to discover and improve vaccine antigens. *Immunol. Rev.*, 199:68-83 (2004).
Blake et al., Parasite genetics and the immune host: recombination between antigenic types of *Eimeria maxima* as an entrée to the identification of protective antigens. *Mol. Biochem. Parasitol.* 138: 143-52 (2004).
Boen et al., Identification of T cell ligands in a library of peptides covalently attached to BLA-DR4. *J. Immunol.*, 165:2040-7 (2000).

Choi et al., Functional mapping of protective epitopes within the rotavirus VP6 protein in mice belonging to different haplotypes, *Vaccine*, 21(7-8): 761-7 (2003).
Currier et al., Spectratype/Immunoscope analysis of the expressed TCR repertoire, *Current Protocols in Immunology*, vol. 2: 10.28.1-10.28.24. Wiley, New York (2000).
Deslauriers et al., Identification of murine protective epitopes on the *Pophyromonas gingivalis* fimbrillin molecule. *Infect. Immun.* 64(20): 434-40 (1996).
Fleischer et al., Reactivity of mouse T-cell hybridomas expressing human Vbeta gene segments with staphylococcal and streptococcal superantigens. *Infect. Immun.* 64:987-94 (1996).
Gomes et al., Comparative analysis of amplified and nonamplified RNA for hybridization in cDNA microarray. *Anal. Biochem.*, 321 :244-51 (2003).
Goyarts et al., Point mutations in the beta chain CDR3 can alter the T cell receptor recognition pattern on an MHC class II peptide complex over a broad interface area. *Mol. Immunol.*, 35:593-607 (1998).
Hanks et al., Rescue of the En-1 mutant phenotype by replacement of En-1 with En-2 Science, 269:679-82 (1995).
Hazbon et al., Hairpin primers for simplified single-nucleotide polymorphism analysis of *Mycobacterium tuberculosis* and other organisms. *Clin. Microbiol.*, 42:1236-42 (2004).
Hechard et al., Molecular cloning of the *Chlamydophila abortus* groEL gene and evaluation of its protective efficacy in a murine model by genetic vaccination. *J. Med. Microbiol.*, 53: 861-8 (2004).
Ivey et al., Identification of a protective antigen of *Coccidioides immitis* by expression library immunization. *Vaccine*, 21(27-30):4359-57 (2003).
Kanagawa et al., Inhibition of MHC class H-restricted T cell response by Lyt-2 alloantigen. *J. Exp. Med.*, 170:901-12 (1989).
Klur et al., Evaluation of procedures for amplification of small-size samples for hybridization on microarrays. *Genomics*, 83:508-17 (2004).
Kuchroo et al., Transfection of TCR alpha-chains into suppressor and T helper cell hybridomas. Production of suppressor factors with predicted antigen specificity. *J. Immunol.* 154:5030-8 (1995).
Letourneur et al., Derivation of a T cell hybridoma variant deprived of functional T cell receptor alpha and beta chain transcripts reveals a nonfunctional alpha-mRNA of BW5147 origin. *Eur. J. Immunol.* 19:2269-74 (1989).
Maeji et al., Multi-pin peptide synthesis strategy for T cell determinant analysis. *J Immunol. Methods*, 134:23-33 (1990).
Martinelli et al., A genetic approach to the de novo identification of targets of strain-specific immunity in malaria parasites. *Proc. Natl. Acad. Sci.USA.*, 102: 814-9 (2005).
Melby et al., Identification of vaccine candidates for experimental visceral leishmaniasis by immunization with sequential fractions of a cDNA expression library. *Infect. Immun.*, 68: 5595-602 (2000).

(Continued)

*Primary Examiner* — Zachary Skelding
(74) *Attorney, Agent, or Firm* — Marshall, Gerstein & Borun LLP

(57) ABSTRACT

The present invention provides a method for identifying a single or group of T cell receptors (TCR) protective and/or effective against a disease, having the following steps: i) obtaining T cells from a donor non-human animal; ii) adoptive transfer of the T cells into a plurality of T cell-deficient recipient non-human animals in a number such that at least one recipient animal is protected against the disease but at least one animal remains unprotected; and iii) determination of the TCR(s) present only in the protected animals. These TCR can be used to identify the determinants or antigens for inclusion in a vaccine or other treatment.

13 Claims, 6 Drawing Sheets

OTHER PUBLICATIONS

Melby et al., *Leishmania donovani* p36(LACK) DNA vaccine is highly immunogenic but not protective against experimental visceral leishmaniasis. *Infect. Immunol.*, 69: 4719-25 (2001).

Pajot et al., A mouse model of human adaptive immune functions: HLA-A2.1-/HLA-DR1-transgenic H-2 class I-/class II-knockout mice. *Eur. J. Immunol.* 34:3060-9 (2004).

Ramage et al., The use of reverse immunology to identify HLA-A2 binding epitopes in Tie-2. *Cancer Immunol.* 55(8): 1004-10 (2006).

Rose et al., Susceptibility to coccidiosis: effect of strain of mouse on reproduction of *Eimeria vermiformis*. *Parasitology*, 88( Pt 1):45-54 (1984).

Sanchez et al., Linear-after-the-exponential (LATE)-PCR: an advanced method of asymmetric PCR and its uses in quantitative real-time analysis. *Proc. Natl. Acad. Sci. USA*, 101:1933-8 (2004).

Scheckelhoff et al., The protective immune response to heat shock protein 60 of *Histoplasma capsulatum* is mediated by a subset of Vbet8.2+ T cells. *J. Immunol.*, 169(10): 5818-26 (2002).

Schirle et al., Combining computer algorithms with experimental approaches permits the rapid and accurate identification of T cell epitopes from defined antigens. *J. Immunol. Methods*, 257: 1-16 (2001).

Schleicher et al., A stable marker for specific T-cells: a TCR alpha/green fluorescent protein (GFP) fusionprotein reconstitutes a functionally active TCR complex. *J. Immunol. Methods*, 246:165-74 (2000).

Shastry, Gene disruption in mice: models of development and disease. *Mol. Cell. Biochem.* 181:163-79 (1998).

Shibui et al., Effects of DNA vaccine in murine malaria using a full-length cDNA library. *Res. Commun. Mol. Pathol. Pharmacol.*, 109:147-57 (2001).

Stemke-Hale et al., Screening the whole genome of a pathogen in vivo for individual protective antigens. *Vaccine*, 23: 3016-25 (2005).

Stirewalt et al., Single-stranded linear amplification protocol results in reproducible and reliable microarray data from nanogram amounts of starting RNA. *Genomics*, 83:321-31 (2004).

Stober et al., From genome to vaccines for leishmaniasis: screening 100 novel vaccine candidates against murine *Leishmania major* infection. *Vaccine*, 24: 2602-16 (2006).

Stone et al., HLA-restricted epitope identification and detection of functional T cell responses by using MHC-peptide and costimulatory microarrays. *Proc. Natl. Acad. Sci. USA*, 102:3744-9 (2005).

Tahara et al., Reconstitution of CD8+ T cells by retroviral transfer of the TCR alpha beta-chain genes isolated from a clonally expanded P815-infiltrating lymphocyte. *J. Immunol.* 171:2154-60 (2003).

Tobery et al., A simple and efficient method for the monitoring of antigen-specific T cell responses using peptide pool arrays in a modified ELISpot assay. *J. Immunol. Methods*, 254:59-66 (2001).

Vidal et al., Differential requirements for CD4 in TCR-ligand interactions. *J. Immunol.* 163:4811-8 (1999).

Villarreal-Ramos et al., Screening gene expression libraries for epitopes recognized in *Mycobacterium leprae* by mouse T cells. *Eur. J. Immunol.*, 21:2621-4 (1991).

Warren et al., Method for identifying microbial antigens that stimulate specific lymphocyte responses: application to *Salmonella*. *Proc. Natl. Acad. Sci. USA*, 87:9823-7 (1990).

Xiang et al., A simple method to test the ability of individual viral proteins to induce immune responses. *J. Virol. Methods*, 47:103-16 (1994).

Yoshida et al., A new method for quantitative analysis of the mouse T-cell receptor V region repertoires: comparison of repertoires among strains. *Immunogenetics*, 52:35-45 (2000).

Zumla et al., Use of a murine T-cell hybridoma expressing human T-cell receptor alpha- and beta-gene products as a tool for the production of human T-cell receptor-specific monoclonal antibodies. *Hum. Immunol.* 35:141-8 (1992).

International Search Report and Written Opinion of the International Searching Authority, PCT/GB2007/004635, European Patent Office, dated Apr. 16, 2008.

International Preliminary Report on Patentability, PCT/GB2007/004635, dated Jun. 8, 2010.

\* cited by examiner

Sequence analysis Vβ4 and Vβ14

| Mse No. | Status | Vβ | CDR3 sequence | Vβ | CDR3 sequence |
|---|---|---|---|---|---|
| 27 | Prot | 4 | FQPPQNFQVDQTPC {7}<br>GADICAKTTPSLSFLPH {4}<br>GQTSVQKPHPPLF {3} | 14 | RRNI {12} |
| 17 | Prot | 4 | FQPPQNFQVDQTPC [19]<br>GADICAKTTPSLSFLPH (3)<br>GQTSVQKPHPPLF {3} | 14 | RRNI {13} |
| 29 | Prot | 4 | FQPPQNFQVDQTPC (7)<br>GADICAKTTPSLSFLPH (6)<br>GQTSVQKPHPPLF {4} | 14 | RRNI {9} |
| 30 | UnProt | 4 | DIFFERENT SEQUENCES {10} | 14 | VST {10} |
| 33 | UnProt | 4 | DIFFERENT SEQUENCES {12} | 14 | VST {10} |
| 26 | UnProt | 4 | DIFFERENT SEQUENCES {12} | 14 | |

FIG. 8

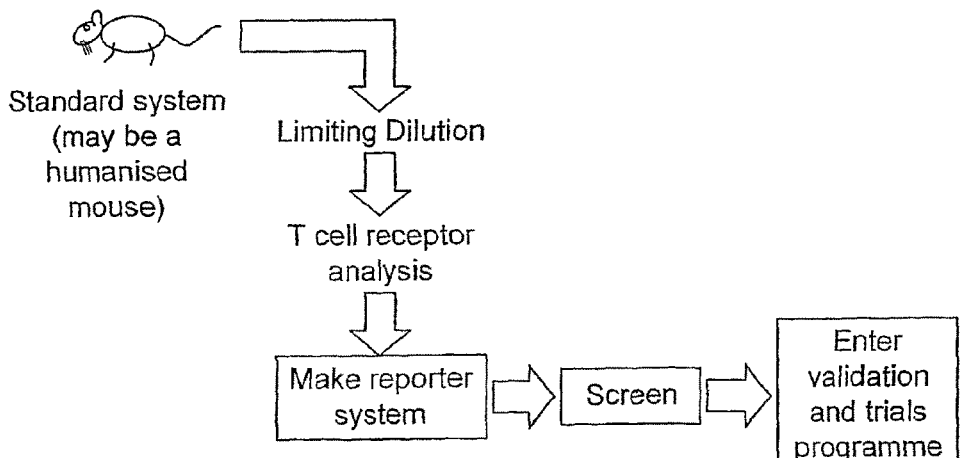

FIG. 9

SEQUENCE LISTING

```
<160> NUMBER OF SEQ ID NOS: 3

<210> SEQ ID NO 1
<211> LENGTH: 14
<212> TYPE: PRT
<213> ORGANISM: Mus musculus

<400> SEQUENCE: 1

Phe Gln Pro Pro Gln Asn Phe Gln Val Asp Gln Thr Pro Cys
1               5                   10

<210> SEQ ID NO 2
<211> LENGTH: 17
<212> TYPE: PRT
<213> ORGANISM: Mus musculus

<400> SEQUENCE: 2

Gly Ala Asp Ile Cys Ala Lys Thr Thr Pro Ser Leu Ser Phe Leu Pro
1               5                   10                  15

His

<210> SEQ ID NO 3
<211> LENGTH: 13
<212> TYPE: PRT
<213> ORGANISM: Mus musculus

<400> SEQUENCE: 3

Gly Gln Thr Ser Val Gln Lys Pro His Pro Pro Leu Phe
1               5                   10
```

METHOD FOR IDENTIFYING A T-CELL RECEPTOR PROTECTIVE AGAINST A DISEASE

This application is the U.S. National Stage of International Application No. PCT/GB2007/004635, incorporated by reference, filed Dec. 3, 2007.

FIELD OF THE INVENTION

The present invention relates to a method for identifying a T-cell receptor (TCR) protective and/or effective against a disease. The TCR may be used to identify an antigen or antigenic determinant for the disease, capable of inducing a protective and/or effective immune response.

BACKGROUND TO THE INVENTION

The concept of vaccination (the inoculation of individuals with pathogen-derived material to induce immunity) has been known since the late 18th century.

Vaccine approaches using either live attenuated or inactive pathogens are undersirable for many reasons, including the risk of reversion to wild-type. For this reason there has been interest in using a "sub-unit" vaccine approach whereby only the key antigenic sequences of the pathogen are included in a vehicle or carrier.

In order to develop a sub-unit vaccine, it is necessary to identify the key antigen(s) in a pathogen. Complex pathogens encode for large numbers of potential antigens (100's-1000's) and this complexity precludes serial testing approaches to identify those antigens that induce protective and/or effective responses.

To date, the master criterion for assessing whether an candidate antigen has potential for use in a vaccine has been its capacity for inducing an immune response. In other words, attention is focussed on those antigens which potentiate the strongest immune response.

However, the induction of a response is not the same as the induction of protection. The immune system is reactive and during an infectious challenge will respond to a large number of antigens. Unfortunately most of the induced responses (especially where the pathogen is antigenically complex) are not effective in controlling the pathogen.

Vaccine candidates which are capable of inducing robust pathogen-specific immune responses and not necessarily protective against disease, e.g. may not protect against subsequent pathogenic challenge (Melby et al (2001) 69:4719-4725; Héchard et al (2004) 53:861-868; Stober et al (2006) as above).

Studies with DNA pool vaccines for antigenically complex pathogens have shown that only a small number of vaccine candidates are protective, and some actually exacerbate disease (Stober et al (2006) Vaccine 24: 2602-2616; Stemke-Hale et al (2005) Vaccine 23:3016-3025; Melby et al (2000) Infection and Immunity 68:5595-5602). When serial fractionation was used to screen vaccine candidates for the fungal pathogen *Coccidioides immitis*, a single protective gene was identified from a cDNA library containing 800-1000 genes (Ivey et al (2003) 4359-4367).

Interestingly, it has been shown that, for antigenically complex pathogens (such as parasites) protective antigens localise to a small number of loci within the genome (Blake et al (2004) Mol & Biochem Parasitol 138:143-52; Martinelli et al (2005) PNAS 102:814-819).

When using immune-response generation as a selection criterion for vaccine candidates, the "response" assays can be refined to assay for so-called "correct" types of response (i.e. the type(s) of immune response which are associated with protection), for example using IFNγ production as an indicator of Th1 T cell response. Although these types of, strategy serve to reduce the numbers of antigens that are identified, the basis of T cell responses is such that most of these T cells that produce the "right kind of response" are not effective in vivo.

Moreover, in many cases effective or protective responses are directed to a small subset of the "responded to" antigens but more than one specificity of response is required for protection.

There is thus a need to identify the effective/protective response within the large repertoire of responding cells generated during an immune response to a pathogen.

There is also a need to identify the antigen(s) responsible for generation of the protective/effective immune response.

STATEMENT OF THE INVENTION

The present inventors have developed an in vivo approach to identify protective/effective immune specificities.

In a first embodiment, the present invention provides a method for identifying a T-cell receptor (TCR) protective and/or effective against a disease, which comprises the following steps:
  i) obtaining T cells from a donor non-human animal;
  ii) adoptive transfer of the T cells into a plurality of T-cell deficient recipient non-human animals in a number such that at least one recipient animal is protected against the disease but at least one animal remains un-protected; and
  iii) determination of the TCR(s) present only in the protected animals.

Since the immune repertoire provided to the recipient animal is restricted, subsequent infection causes the generation of a clonally restricted immune response. In other words, the immune response generated in a protected animal having received a restricted immune repertoire contains a greater proportion of protective/effective T cells than that generated by an animal having a complete repertoire. Using the method of the invention, therefore, since the total TCR portfolio is reduced, it is possible to distinguish between protective/effective and non-protective/ineffective responding T cells and thus determine those TCRs which mediate protective/effective immunity.

The present approach has the advantage over in vitro screens that it focuses entirely on protective/effective T cell responses, rather than all antigen-stimulated T cell responses. It therefore provides invaluable information on the TCRs which are protective and/or effective against the disease.

The TCRs identified by the method of the invention may be used to identify the antigen(s) which elicit a protective and/or effective response. The TCRs (or sequences thereof) can thus be used to screen for the "relevant" antigen sequences.

In a second aspect, the present invention provides a method for screening for an antigen or antigenic determinant which is capable of inducing a protective and/or effective immune response, which comprises the following steps:
  (i) identification of an protective and/or effective TCR by a method according to any preceding claim;
  (ii) production of a cell expressing the protective/effective TCR;
  (ii) use of the TCR-expressing cell to screen candidate antigens/antigenic determinants
  (iv) selection of an antigen/antigenic determinant recognised by the protective/effective TCR.

The antigen may be derivable from the pathogen. Alternatively, the antigen may "mimic" a pathogen-derived antigen (or part thereof) but be chemically dissimilar.

In a third aspect, the present invention provides a method for making a sub-unit vaccine, which comprises the following steps:
  (i) identification of one or more effective antigen(s) or antigenic determinant(s) by a method according to the second aspect of the invention;
  (ii) incorporation of the antigen(s)/antigenic determinant(s) in a sub-unit vaccine.

In a fourth aspect, the present invention provides a TCR protective and/or effective against *Eimeria* infection which comprises one of the following TCRVβ CDR3 sequences:

```
FQPPQNFQVDQTPC       (SEQ ID NO. 1)

GADICAKTTPSLSFLPH    (SEQ ID NO. 2)

GQTSVQKPHPPLF.       (SEQ ID NO. 3)
```

In a fifth aspect, the present invention provides use of a TCR according to the fourth aspect to screen for an antigen or antigenic determinant which is capable of inducing an immune response protective and/or effective against *Eimeria* infection.

DESCRIPTION OF THE FIGURES

FIG. 8 Identity of TCRVβ CDR3 sequences (amino acid) of TCRVβ4 and TCRVβ14 from three protected and three non-protected mice.

FIG. 9 is a schematic diagram showing a generic protocol for antigen identification.

DETAILED DESCRIPTION

Figure 1A:
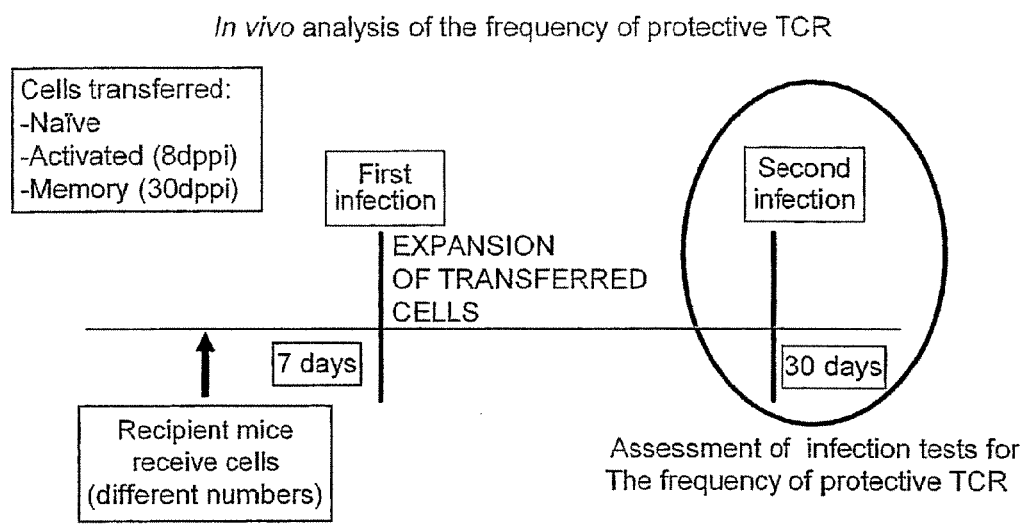
FIG. 1A is a graph illustrating the protective effect of adoptive transfer of lymphocytes from, naïve, responding and recovering donor mice to T-cell deficient recipients.

The first aspect of the present invention relates to a method for identifying a T-cell receptor (TCR) protective and/or effective against a disease by adoptive transfer of a limited number of T cells from a donor animal to a recipient animal.

Donor Animal

The donor animal is an animal which comprises protective and/or effective T cells amongst its complete T cell repertoire.

The donor animal may be a naive animal (i.e. an animal previously unsubjected to disease or antigenic challenge).

The donor animal may be treated to expand the number of circulating T cells. This may be done by, for example treatment schedules or "vaccine strains", which will cause appropriate stimulation of the immune system, and an associated expansion of the T cell population.

The animal can be challenged with disease or an antigen preparation associated with the disease, this should cause "specific" T cell expansion and increase the proportion of potentially relevant cells in the total lymphocyte population.

The animal may, for example, be challenged by direct infection (as has been done for the *Eimeria* pathogen, shown in the Examples), or given a preparation of attenuated organism or other crude vaccine preparation.

Preferably the animal is "actively responding", i.e. in the process of generating an immune response to the pathogen or an antigen preparation thereof.

Alternatively the animal may be "recovered". i.e. one which has previously generated an immune response to the pathogen or an antigen preparation thereof but which is no longer actively responding.

If the appropriate T cell population is expanded, this should mean that it is possible to confer protection on a T-cell deficient recipient by adoptive transfer of fewer transferred cells. It is also easier to find an appropriate transferred cell number (TCN) at which only a small proportion (say 10-20%) of recipient animals are protected.

It is likely that different protective/effective T cells will be generated in different donor animals due to the stochastic nature of the immune response. If it is desirable to define as many antigenic determinants and/or as many protective/effective T cells specificities as possible then a plurality of donor animals may be chosen. Alternatively, if the goal is to define the, or the minimal number of, TCRs responsible for immunity, then it is preferable to use a single donor animal to allow direct comparison of recipient animals and to avoid over-complication of the system.

Recipient Animal

The recipient animal is "T-cell deficient" in that it has effectively no endogenous T cells.

T-cell deficient animals may, for example, be TCR or RAG knockout, SCID or "nude" animals.

A limited number of T cells are transferred from the donor animal to the recipient animal. Recipient animals may then be given a T-cell expansion treatment such as an infection (with live or attenuated pathogen or preparation thereof) or an uncharacterised vaccine preparation.

Complex expression libraries may also be used as a vaccine for the expansion treatment (1, 20).

After a given period of time (such as 1 month) recipient animals are challenged with the wild type pathogen and assessed for resistance/susceptibility at an appropriate time post-challenge.

The donor and recipient animals may both be transgenic for human MHC. The animals may be transgenic for human class I and/or human class II MHC. This has the advantage that there is evidence to suggest the precise peptide specificity of the T cell response will more accurately represent the human response (i.e. the animal will respond to the same epitopes as in a human immune response).

Transferred Cells

T cells from the donor animal are adoptively transferred to the recipient.

The T cells may be transferred as part of a population of cells (such as part of the cell or tissue sample obtained from the donor mouse). The cell sample obtained from the donor mouse may be treated to increase its proportion of responding T cells, or a particular type of T cell.

For example, the cell sample may be sorted (e.g. by FACS or using magnetic beads) "positively" (for T cells) or "negatively" (to remove other cell types).

T cells may be selected by, for example, their expression of TCR, CD3, CD4 or CD8.

T-cells transferred to the recipient may represent a subset of the total T cells from the donor animal. For example, the population may be sorted for CD4+ or CD8+ T cells. This may be advantageous if it is already known that one or other type of response is associated with protection in vivo.

The population of cells may be stimulated ex vivo in order to increase the proportion of T cells or potentially relevant T cells.

Transferred Cell Number (TCN)

The T-cell-comprising cell sample derived from the donor animal is transferred to the recipient animal. The cell sample should represent an incomplete or restricted T cell repertoire. The repertoire should be sufficiently restricted such that the expanded T cell population (after subsequent infection or antigenic challenge) is dominated by a relatively small number of effective/protective TCRs. The numbers of protective/effective TCRs (which may, for example be fewer than 50, 40, 30, 20 or 10 per protected animal) should be low enough that sequencing of all the TCRVβ sequences is practically feasible.

In the method of the first aspect of the invention, T-cells may be transferred to recipient animals in a number such that at least one animal is protected from the disease, but at least one animal remains unprotected. The TCN is thus at the threshold between the number of transferred cells where substantially all recipient animals will be protected and the number where too small a proportion will be protected (meaning that, in the number of animals used in the experiment, no protected animals may be generated).

It is desirable for a relatively low proportion of the animals receiving a given TCN display the protected phenotype. This minimises the number of transferred T-cells responsible for protection and thus simplifies the picture when it comes to identification of individual TCRs. For example, the TCN may be chosen such that at least one, but less than 50%, 40%, 30%, 20% or 10% of the recipient animals display the protected phenotype.

Preferably two or more recipient animals are protected, so that their pattern of TCR expression can be compared.

In order to establish the optimal TCN for a given system, one can perform a limiting dilution analysis. In this way, recipient animals may be given donor cells at varying TCNs (such as ranging between 10 and 100 million cells). The optimal TCN may then be chosen as the one (or the lowest one) resulting in protection of, for example, 10-20% of recipient animals.

As an alternative to carrying out a separate step to define the minimal number of T cells that can confer immunity, the experiment may be performed with large numbers of recipient animals at each of a small range of TCNs (such as 100, 300, 1000 and 5000 cells). Protected animals taken from the lowest number of cells required to afford protection could then be directly used to define the protective and/or effective TCR(s).

The definition of "protected" will vary depending on the disease and animal model. In general a protected animal will show reduced propensity to succumb to a disease, decreased severity of disease, in appreciable improvement in disease symptoms or a decrease in pathogen load when compared to non-protected equivalent animal.

In the *Eimeria* system, an animal was considered to be "protected" when it produced statistically significantly fewer oocysts than TCR-deficient animals that received no cells.

The TCN may be fewer than 5000, 1000 or 500 T cells per recipient animal.

Analysis of Protective/Effective TCRs

In order to identify the TCR(s) protective/effective against the disease, the TCRs present in the protected animals are determined.

This may be accomplished, for example, by comparing the TCRs expressed in the protected versus the un-protected recipients.

Cells may be stimulated prior to anaylsis ex vivo, for example using crude antigen preparations or live pathogens. They may also be stimulated to increase the proportion of CD4+ or CD8+ cells, or sorted to separate these two subpopulations (so that only one cell type may be considered, or so that the two cell types may be considered independently).

T cells (such as splenic T cells, or T cells from the lamina propria, intraepithelial compartments or mesenteric lymph nodes) may be harvested from protected and non-protected mice and then TCRVβ expression analysed by PCR and sequence analysis. TCRVβs which are interesting from the point of view of being from candidate "protective" TCRs are those that are expressed in a protected recipient, but not in or are underrepresented in the non-protected recipients. Of particular interest are TCRVβs showing only a single sequence within a recipient animal (indicating monoclonality) or between two or more recipient animals (indicating general association of this TCRVβ sequence with the protected phenotype).

TCRα

In order to identify the complete TCR, it is desirable to isolate the TCRVα chain from the same cell as the "protective" TCRVβ.

This may be done using techniques known in the art such as using FACS or magnetic sorting using Vβ-specific antibodies (an indicated by Vβ molecular analysis) followed by PCR to identify the TCRVα chain.

If the TCRVα chain is difficult to isolate, the TCRVβ can be used to make a transgenic animal which will associate with various TCRVα in the thymus during development. The TCRVα chain can be isolated from these animals, using a response- or protection-based assay. Alternatively the TCR transgenic containing the known TCRVβ can be used without knowing the TCRVα chain.

An alternative approach is to perform ex vivo cloning of T cells followed by TCR Vβ screening of the resulting clones.

Cells Expressing TCRs

Once the TCRVα and β are known, transfectants may be made expressing the TCR by standard techniques. For example, the genes may be transfected into a suitable recipient cell line to give a TCR-expressing reporter cell.

The TCRVα and β sequences (or just the TCRVβ sequence—see previous section) can be used to make a transgenic non-human animal expressing the TCR. These animals provide a source of cells for antigen screens.

Another option is to use the original cells derived from the protected recipient animal, from this the TCRVβ sequence was derived. For example, the initial stock could be used to make a T cell hybridoma, to obtain a stable TCR-expressing cell line.

Antigen Screen

In a second aspect, the present invention provides a method for screening for an antigen or antigenic determinant effective in inducing an effective/protective immune response.

In an adaptive immune response, T lymphocytes are capable of recognising peptides derived from a protein antigen. Antigen presenting cells (APC) take up protein antigens and degrade them into short peptide fragments. A peptide may bind to a major histocompatability complex (MHC) class I or II molecule inside the cell and be carried to the cell surface. When presented at the cell surface in conjunction with an MHC molecule, the peptide may be recognised by a T cell (via the T cell receptor (TCR)), in which case the peptide is a T cell epitope.

The screening method may be used to define the epitope recognised by the protective/effective TCR. Alternatively, the screen may identify the antigen (or part thereof) which comprises the recognised epitope, without precisely defining the epitope itself.

An antigenic determinant is a part of an antigen responsible for T cell activation.

The screen may be used to identify candidate antigens in, for example, complex mixtures of antigens (which may be fractionated), expression libraries or combinatorial chemistry-based peptide libraries (to find a mimic peptide).

Disease

The method of the invention can be used for any disease for which (i) a reasonable animal model of disease exists, and
(ii) T cell specificity is an effective part of the disease process.

All infectious, allergic, autoimmune and tumour diseases which can be adapted to an animal system are suitable targets for the system. The terminology used herein is generally applicable to infectious diseases. However, as would be clear to a person skilled in the art, to apply the system to other diseases (such as allergies, autoimmunity etc) may necessitate use of an alternative (but analogous) term. For example where an antigen for an infections disease may be derived from the pathogen, for an allergy it may be an allergen and for an autoimmune disease it may be an auto-antigen.

Target human infectious diseases include:
Herpes simplex virus (HSV)
*Chlamydia* spp.
Cytomegalovirus (CMV)
Respiratory syncytical virus (RSV)
*Listeria monocytogenes*
*Staphylococcus aureus*
*Candida albicans*
*Mycobacterium* spp.
*Leishmania* spp.
*Plasmodium* spp.
*Trichuris* spp.
*Cryptosporidium* spp.
*Toxoplasma gondii.*

The term "protective" is used to indicate that the antigen causes or the T cell mediates are immune response which protects against or is effective against the disease. The effect may be thus prophylactic, therapeutic, or both.

Protocols

A generic procedure is outlined in FIG. 9. The situation will be described for identification of protective and/or effective T cells against a generic pathogen but the process can be modified to identify T cells that effect allergy, autoimmunity or tumour rejection.

Phase 1: Establishing the "Protective/Effective Unit"

The optimal first step is to define the minimal number of T cells that can confer immunity after the expansion phase. This is achieved by limiting dilution adoptive transfer. This phase can be omitted and the process time limited by the execution of an experiment with large numbers of recipient mice at cell transfer numbers of 100, 300, 1000 and 5000 T cells and taking mice from the lowest number of cells required to afford protection. The aim is to use a cell number that protects approximately 10% of the recipient mice. The actual number of cells may differ according to infectious system and the time at which the cells are taken from the donor mouse. With most infections the time at which most efficient transfer of T cells is already defined in the literature but if not available this can easily be defined by experimental transfer with large cell numbers (e.g. $10^7$ cells). It is most useful to use a single donor mouse for each experiment since the stochastic nature of immune induction will generate different protective/effective T cell clones in different individuals. Indeed, the technology is not about defining every T cell specificity that can give effect but will define the minimal group of T cell receptors that are required for immunity. This is an important added benefit for the technology since it will define the number of specificities (and antigens) that need to be included in a successful sub-unit vaccine.

Other useful information can include the a priori knowledge of the relative importance of CD4+ or CD8+ T cell responses in the expression of effect (e.g. protection). This information is often available from the literature but is not a prerequisite for the study. An example of the value of this analysis would be to restrict analysis to the most effective cell subset either by sorting the cells prior to adoptive transfer or by sorting the cells post identification of protected animals. The latter approach may be more time consuming but will allow identification of effective TCR from both CD4+ and CD8+ cells. Where interactions between these cell subsets are complex then the effective minimal repertoire may be larger than where single cell populations are chosen by being based upon the combined frequency of both populations of cells. In these circumstances the analysis may require more sequencing effort. Downstream antigen identification is influenced by the type of T cell expressing the effective TCR and represents further added value.

Phase 2: Defining Restricted Repertoire in Protected and Non-Protected Animals

Small numbers of T cells are taken from actively responding donor mice and adoptively transferred into T cell deficient recipient mice (e.g. TCR(β×δ)−/− or RAG1−/− or nude or SCID mice). Mice are given a T cell expansion treatment that may be an infection (as described above with an attenuated pathogen or a drug-treatment schedule) or an uncharacterised vaccine preparation. After a suitable period (for example approximately 1 month) recipient mice are rechallenged with wild type pathogen and assessed for resistance/susceptibility at an appropriate time post challenge. Protection is assessed by statistical comparison of individuals with a group of 10-20 mice that did not receive T cells (actual number will depend upon the pathogen or other system). The number of transferred T cells is optimal with between 10% and 20% of the animals exhibiting protection against infection as this allows identification of minimal T cell populations that confer effect/ protection with a large proportion of mice that are T cell intact but not protected. The number of protected mice required depends upon the nature of the protective and/or effective repertoire but this is unlikely to be above 10-15 individual mice (with the *Eimeria* system this analysis is possible with as few as 3 protected mice within an experiment).

Phase 3: Analysis of Protective and/or Effective TCRVβ Repertoires

This phase of analysis involves the harvesting of splenic T cells from protected and non-protected mice which, if appropriate, may be magnetically separated into CD4 and CD8 subsets for further analysis. The cells are divided into three groups; one group is processed for molecular analysis by disruption in RLT or similar buffer, a second batch is frozen in liquid nitrogen for possible downstream analysis and a third is serially transferred into T cell deficient mice "parked" (for future verification of the "protective" phenotype). A small aliquot of cells from each mouse is assessed by FACS analysis to ascertain the proportions of T cells present in each recipient.

Molecular Analysis

The samples of disrupted cells are stored frozen in aliquots. Batches of cDNA are made using oligo-dT and/or T-cell receptor constant region primers. These cDNA samples are assessed by PCR for the presence of different TCRVβ using primers designed to amplify each of the murine TCRVβ-TCRCβ products and visualised by agarose gel electrophoresis. Positive PCR products are cloned into the TEasy plasmid and used to transform a suitable strain of E. coli and plated on appropriate selective media. In the first instance, twenty positive bacterial colonies are picked and sequences of inserts obtained using appropriate primers (e.g. the TCRCβ primer). The initial analysis is performed on all "protected" individuals and on selected (preferably at least 6) "non-protected" individuals. This sequence data determines the identity of T cell clones that exist in both populations of protected and non-protected individuals.

Cellular Analysis

The information from the molecular analysis is used to inform on the best strategy for the subsequent cellular analysis. The aim of the cellular analysis is to isolate the TCRVα chain in the same cell as the identified TCRVβ chain.

For example, where a protection-associated TCRVβ is monoclonal or dominated by a single clone then cells from the serial transfer "parked" cells or frozen stocks can be subjected to FACS or magnetic sorting with Vβ-specific antibodies. The cellular analysis can also involve the rapid cloning of the "protection associated" T cells, screening for the exact TCRVβ by PCR and then using this sample to identify the TCRVα chain. The stimulus for the cells depends upon the cell type (CD4 or CD8) under consideration and the pathogen being considered. This involves ex vivo stimulation with either crude antigen preparations, or live pathogens. Having both chains of the TCR allows the production of transfectants with the exact TCR isolated in the experiments. These represent the targeted screen based upon known capacity to afford protection.

In More Detail:

Vα Identification

1. Samples

At the time of sample collection lymphocyte populations (spleen, lymph node and possibly other immune tissues) the cells may be divided into three sample groups, the first for TCRVβ analysis, the second frozen in liquid nitrogen for subsequent resuscitation and the third serially transferred (parked) into further recipient animals (the third is optional). After protective TCRVβ repertoires have been identified the process to identify TCRVα is aided by analysis of samples 2 and 3.

2. Vα Analysis

Once the protective TCRVβ is known then frozen or "parked" cells can be separated by fluorescent activated cell sorting (FACS) using TCRVβ family specific antibodies thereby providing a restricted population of starting cells. If the number of "protection-associated" TCRVβ sequences is low (<3) then it is possible to use primers to identify all of the TCRVα associated with the population and use subsequent paired transfection methods to identify the appropriate TCRVβ TCRVα pairings. Alternatively, the appropriate TCRVβ+ cells can be sorted by FACS and deposited as single cells into wells of a microtitre plate. The cells can then be analysed directly by single cell RTPCR or expanded by antigen-specific triggers or by non-specific stimuli such as plate-bound anti-CD3 or mitogen.

The cells can be expanded by traditional T cell cloning methodologies (optimally using antigen-presenting cells derived from T cell deficient animals). T cells derived by classical cloning and in vitro maintenance on mixed antigen preparations can be directly used in an antigen screen (see next section).

The analysis begins with identifying the appropriate TCRVβ sequence from the clonal wells (either single cell or monoclonal expansions); this may require more than one round of PCR, especially from the single cell. The first round of RTPCR and PCR may involve the use of conserved, degenerate or specific primers in TCRVα, TCRCα and TCRVβ, TCRCβ sequences or single primer based linear amplification (3, 5) or similar method to generate sufficient product for analysis in a subsequent PCR reaction (6, 21). Once the appropriate cells have been identified then an RTPCR approach can be used to identify the TCRVα sequence that derives from the same cell.

The first step in the TCRVα analysis is amplification of the TCRVα by standard techniques (the amplification step may be done at the same time as amplification for TCRVβ. The identity of the TCRVα that are present in cells expressing the "right" TCRVβ can take the form of a simple PCR approach using primers either degenerate or specific primers for example those described previously (3, 5). Alternatively, further TCRVα primers can be designed and applied to the analysis. Products of the PCR can be cloned into a suitable vector and used to transfect E. coli before sequencing of plasmids in multiple colonies using standard DNA sequencing methodologies.

An alternative approach involves the initial identification of the correct TCRVα or TCRVβ present in linear or non-specific amplified samples using a method that includes application of samples to solid-phase bound TCRVβ-specific oligonucleotides and detection of the bound sample. The detection system may involve incorporation of biotinylated nucleotides or otherwise labelled nucleotides in the amplification step and detection using enzymatic, fluorochrome based or other similar technology (e.g. 9, 12, 17, 29). Once the correct TCRV families had been identified then specific PCR primers can be used with an aliquot of the original sample to generate TCRVα or TCRVβ CDR3 sequences which can then be sequenced directly or cloned into an appropriate vector and transformed into E. coli prior to colony selection and sequencing.

The TCR may be transfected into any reporter cell system that would lead to signalling after antigen presentation to the transfected TCR. TCR transfection may be achieved by standard techniques (2, 4, 7, 13, 18, 25, 30). The recipient cell may be a hybridoma (11, 14), or a thymoma (such as the s49.1 thymoma from ATCC). If the recipient cell is CD4-ve and CD8-ve (such as a TCR deficient derivative of DO11-10) CD4 or CD8 needs to be transfected alongside the TCR containing vector (25). Functionality of transfected TCR has also been demonstrated using a retroviral vector (23).

Transgenic Animals

If the TCRα chain is more difficult to isolate, then the sequence of the TCRVβ can be used to create transgenic mice which express the appropriate TCRVβ and these will associate with TCRVα during development in the thymus of the transgenic mouse. The phenomenon of allelic exclusion which operates at the TCRVβ locus will dramatically limit the expression of endogenous TCRVβ and either the appropriate TCRα chain can be isolated from these mice or the cells may have protective/effective capacity without knowing the TCRVα chain. In the latter case the cells may be used directly from the TCRβ transgenic mouse.

The production of transgenic animals can be done with standard transgenic protocols (10) or using ES cells made into a knockin system targeting the transgene to the TCRβ locus (8, 19).

The final reporter system can be made in the form of a double transgenic with both TCRα and TCRβ chains and backcrossed onto a RAG1−/− or RAG2−/− background. The backcross to RAG−/− is advantageous because although allelic exclusion occurs at the TCRβ locus it does not occur at the TCRα locus hence endogenous rearranged TCRα can be a problem without this background (which stops all TCR and Ig recombination).

In Vivo Confirmation of the Identification of Protective/Effective T Cell Populations In order to verify the identification and protective/effective capacity of T cells, serial adoptive transfer of cells from previously identified "protected" and "non-protected" individuals may be performed. The methodology is essentially as described for the work with *Eimeria vermiformis*. Briefly, cells are transferred from all protected and some (3 to 6) non-protected mice into at least 5 recipient mice which are then rechallenged with pathogen to assess the continued efficacy of the cells under parallel molecular analysis. The cells in these animals may also serve as a source of material for the cellular studies outlined in the previous section and represent a further expanded population of cells that can provide archived material (frozen cells, DNA and RNA) for downstream studies identified by the parallel molecular analysis.

The Use of Known Protective/Effective TCR Genes as an Antigen Screen

The aim of the system is to identify T cell receptors that associate with protection or effect, thereby allowing substantial refinement of downstream searches for appropriate antigens. The molecular identification of TCR allows either the creation of T cell transfectants or the generation of TCR transgenic animals as a source of cells for standard antigen screens. The specific system will depend upon the pathogen/disease and T cell subset under investigation but is based upon technologies that are routinely used in academic and commercial screening for antigens that stimulate T cells. Quite simply, the system makes the screen identify the appropriate and effective antigen for inclusion in vaccines or immunotherapeutic schedules. The screens may involve the fractionation of complex mixtures of antigens, the use of expression libraries or the use of combinatorial chemistry-based peptide libraries (in this case finding a mimic peptide).

In More Detail:

Antigen Screening

1. TCR Recognition

In order to determine which antigen is recognised by a TCR, an antigenic determinant (usually a peptide, but may be a modified peptide or even non-peptide based mimetic) needs to be presented by an appropriate MHC molecule.

TCR is expressed either on a T cell or another suitable cell such as a transfectant (see above) and an activation assay may be used as a reporter system (e.g. assaying for cytokine production). One consideration is the presentation pathway required for presentation to the TCR. For most TCRαβ T cells, the TCR are either restricted to MHC class I (CD8+ T cells) or MHC class II (CD4+ T cells). The MHC class I presentation pathway presents endogenously processed antigens derived from the cytosol whereas the MHC class II pathway presents exogenous antigen derived from outside the cell and processed in specialised endosomes. With some cell types such as dendritic cells a phenomenon known as cross-priming can occur whereby exogenous antigens are trafficked into the endogenous pathway and loaded onto MHC class I. For most response detecting T cell assays (or TCR recognition) the antigen needs to be presented to the responding T cells by appropriate antigen presenting cells via the correct pathway. For CD8+ T cells, antigen is presented via a cytosolic route into the MHC class I pathway. This may be achieved experimentally by transfection of antigen encoding sequences into a target cell that expresses the right MHC class I molecule. Since almost all cells can process via the MHC class I presentation pathway the choice of target cell is broad (as long as the responder cell is appropriately armed to respond (there are various rules of engagement for naïve and responding T cells that may need to be taken into account)). CD8+ T cells can be assayed by cytokine production, changes in cell surface markers, cell division or capacity to kill target cells. This may be similar or involve other systems in a transfectant or hybridoma system which may also include an appropriate marker/reporter system. Often TCR transfectants or T cell hybirdomas act as if they are already partially activated and have a less stringent activation requirement (e.g. not require pre-priming).

The methods for screening for CD8+ T cell associated TCR may involve, for example:

a) the establishment of a cytosolic expression library of potential antigens in a cell with the correct MHC (may be supplied by transfection to the target cell).

b) the use of peptides (that may be predicted or random overlapping) from the target antigen that are then used to pulse cells with the right MHC in such a way as to replace the peptides on the surface expressed MHC c) the use of peptides in the context with soluble recombinant MHC molecules (usually in the form of a multimeric reagent e.g. tetramer) which can then be assayed either by TCR driven function or by FACS (the tetramer reagents can be used in this way). The tetramers can involve refolding assays from random pools which are then reacted with the cells with clonal TCR and then isolated, the peptide rederived and sequence of the peptide determined by protein sequencing methods and/or Mass spectrometry.

d) The use of peptide loading or soluble MHC methods in conjunction with combinatorial libraries of peptides (this would not find the pathogen peptide but can find a mimic).

e) the use of whole antigens added to appropriate cells (e.g. DC) that can mediate cross-priming and present in the MHC class I pathway (in this way the methods used to screen for MHC class II responding cells can be adapted for MHC class I (see below for example methods)

The methods for screening for CD4+ T cell associated TCR may involve, for example:

For CD4+ T cell associated TCR the antigen is normally presented by the MHC class II pathway and if a cell is involved then this cell needs to express the appropriate MHC (can be engineered by transfection) and should possess appropriate pathways for depositing the antigen in a format for binding to MHC class II (in the case of whole antigen exposure)

a) The preparation of proteins from stage(s) of the pathogen may be separated using a series of standard molecular separation methods including chromatography (e.g. anion exchange), gel filtration, preparative electrophoresis or other separation methodologies. The fractions of the antigen preparation are then applied to appropriate antigen presenting cells and the response assessed by exposure to cells expressing the TCR of interest (will probably also need to be CD4+).
b) The creation of cloned expression libraries which can secrete the antigens of interest and then the supernatants can be tested in assays with appropriate antigen presentation cells (APC) and the reporter cell.
c) The creation of cloned expression libraries where lysates are obtained from antigen expressing clones and then these are used as exogenous antigen applied to APC and the reporter cells.
d) The use of combinatorial peptide libraries with appropriate features for MHC class II binding.
e) The use of peptide prediction to identify potential peptides from within the pathogen genome, synthesis of peptides and screening using MHC class II+ APC and reporter cells.
f) The use of peptide-libraries with physical linkage to the MHC class II molecule (2)(15, 22, 24, 26-28)

The Adaptation of the System with Humanised Mice

The studies outlined above allow the identification of known protective/effective T cell receptors and the identification of the antigens/peptides that stimulate these T cells of known effectiveness. The biology of protection is such that a number of features determine the capacity of any antigen to protect. These include expression in the pathogen at the right time, availability for the immune response and the ability of the immune response to process and present the antigen. While many aspects of antigen biology are addressed by the core technology, one aspect of this system can be improved by the construction of two transgenic mice that express human MHC components in the place of murine MHC components. It has recently been shown (Pajot, et al (2004). Eur J Immunol 34:3060-9) that when human MHC molecules are expressed by mice in the absence of endogenous MHC molecules then the precise peptide specificity of the response is identical (not just on the same antigen) to that seen in humans with those MHC molecules in response to challenge with Hepatitis C virus.

The two mouse strains required for the humanised system are:
(i) donor mouse with the humanised MHC class I and II in a mouse MHC class I and II-deficient background; and
(ii) recipient mouse, identical to the donor, but on a T cell deficient background (e.g. TCR or RAG knockout, SCID or nude).

In more detail:

Humanised Mice

Known humanised MHC mice (16) can be made more useful for the purposes of the present invention by direct targeting of the transgenes into particular parts of the murine genome to generate direct replacements for components of the mouse MHC system.

The Donor Mice

The donor mouse is transgenic for the human MHC class I-β2m and MHC class II molecules on a mouse background deficient in endogenous β2m and endogenous MHC class II [termed hMHC tsg mMHC KO]. The optimal (but not only) strategy is to target the human MHC transgenes into the relevant β2m and MHC class II loci of the mouse by targeted mutagenesis (gene replacement by knockout/knockin strategy in ES cells used to generate the mice). This dramatically simplifies the breeding strategies needed to maintain and produce the colonies required. For example, a human MHC class I molecule/human β2m hybrid molecule can be targeted into the mouse β2m locus (thereby removing all endogenous mouse MHC class I molecules). Similarly, a human MHC class II gene can be targeted into a mouse MHC class II gene.

The Recipient Mice

The recipient mice are the same as the donor mice in the status of human and mouse MHC genes but bred onto a T cell deficient or T and B cell deficient background (e.g. SCID, nude, RAG1, RAG2, TCRβ or TCRβ×δ). These mice are termed [T deficient-hMHC tsg mMHC KO] to identify them for the purpose of explaining the system.

The Protecta System in Humanised Mice

The donor [hMHC tsg mMHC KO] mice are infected with the pathogen of choice to stimulate a strong immune response. T cells derived from the appropriate organ (usually lymph node or spleen), may be sorted to extract individual cell populations (e.g. CD4+ or CD8+ or "activated cells") before dilution to an appropriate cell number and administration to recipient [T deficient-hMHC tsg mMHC KO] mice. Recipient animals are treated in the same way as for the standard system i.e. the cells are stimulated to expand by infection/immunisation/exposure and after approximately 1 to 2 months a challenge is performed with the infection (or other challenge system) under investigation. Subsequent analysis of the "protected" and "non-protected" animals and the cells present in these animals will follow the standard methodology described above and in the examples.

The invention will now be further described by way of Examples, which are meant to serve to assist one of ordinary skill in the art in carrying out the invention and are not intended in any way to limit the scope of the invention.

EXAMPLES

Example 1

Restriction of the T Cell Repertoire In Vivo

The enteric apicomplexan protozoa, Eimeria spp., represent an important group of livestock pathogens. The Eimeria spp are phylogenetically related to a wide group of human pathogens including Plasmodium (causes malaria), Toxoplasma gondii and the enteric parasite Cryptosporidium parvum. The genome of the eimerian parasites is approximately 60 Mbp and the apicomplexan parasite genomes have been estimated to encode 7,000-10,000 gene products, all of which are potential antigens. Infection with the eimerian parasites induces immunity against rechallenge infection which is particularly strong and long-lived. The nature of the protective and/or effective response against many apicomplexan parasites is well established as dependent upon the capacity of T cells to kill intracellular pathogens.

This experiment investigates the nature of the protective/effective and responding T cell repertoires during infection with Eimeria vermiformis, a natural parasite of the mouse. It is thought that the nature of the responding repertoire to this pathogen is highly complex and polyclonal as judging by TCRVβ expansions and assessment of CDR3 length polymorphisms (by immunoscope).

In order to investigate the relevant specificities within this repertoire, the inventors have developed a method whereby T cell deficient recipient mice are given a limited repertoire of lymphocytes from primed donor animals.

The procedure is to adoptively transfer different numbers of cells into groups of approximately 6-10 mice and to infect the recipients twice with *E. vermiformis*. One characteristic of the *E. vermiformis* system is that the infection is self-limiting and the maximal reproductive capacity of the parasite is encoded within the parasite genome. This aspect of the biology allows the challenge of highly immunodeficient animal without serious clinical consequences (in other systems this priming treatment can be achieved with a variety of schedules e.g. by using drug termination). The numbers of parasites produced during infection is a direct consequence of the degree of immunity and during the first challenge the system is testing how many cells are required to confer immunity. The first infection also stimulates expansion of the transferred cells such that when the animals are rechallenged (one or two months later) the degree of immunity is related to the number of different TCR's (i.e. repertoire) rather than number of cells transferred.

Figure 1B:
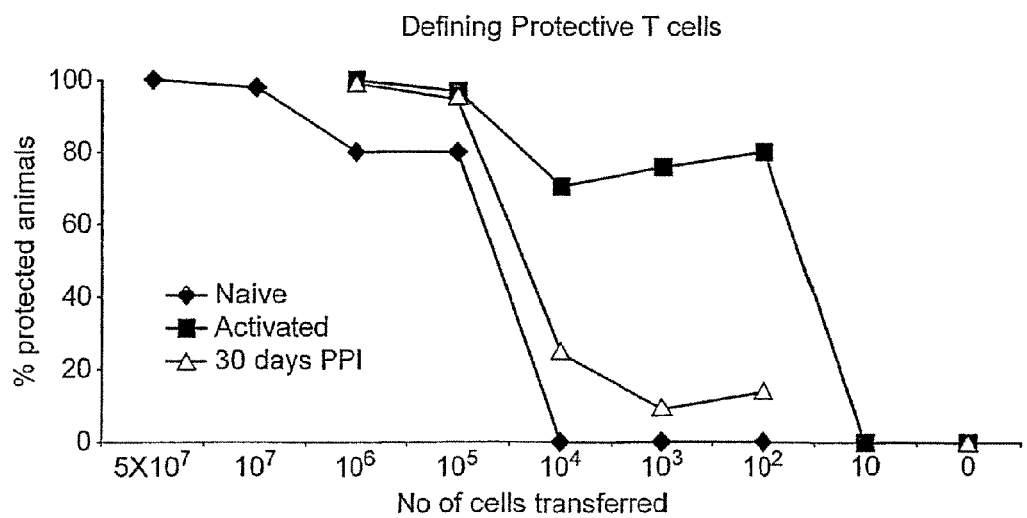
FIG. 1B is a schematic diagram showing a generic protocol for the in vivo analysis of protective TCR.

The experimental strategy is depicted in FIG. 1. A mixture of spleen and mesenteric lymph node cells are transferred from C57 BL/6 mice that are either naïve or actively responding (10 days post primary infection; dppi) or recovered from infection (30 dppi). Single cell suspensions were obtained by physical disruption of spleen and mesenteric lymph nodes of intact C57 BL/6 (6-8 week old, female) from mice that had not received infection, 10 days dppi with 50 *E. vermiformis* sporulated oocysts or recovered mice ~30 dppi with 50 *E. vermiformis*. Red blood cell contamination is removed by "flash lysis" with sterile distilled water and the numbers of viable lymphocytes are assessed microscopically using Trypan Blue exclusion. Aliquots of cells are prepared at appropriate concentrations and administered by intraperitoneal injection (in 200 µl/mouse) into TCR(($\beta \times \delta$)-/- recipient mice (7-10 recipients/group).

One week post-transfer, mice are challenged with 50 *E. vermiformis* oocysts and infection monitored by microscopic analysis of faecal oocyst output according to standard methods (31). [This infection is monitored to ensure infection of all mice, it does not represent an analysis of effective repertoire. The first infection serves to expand the numbers of T cells capable of responding to *E. vermiformis* antigens]. The test for effective repertoire is afforded by a second challenge infection (50 oocysts) of the recipient mice at ~30 days post first infection. The magnitude of infection was monitored by enumeration of faecal oocyst output as described previously (31).

At the point of assessment of repertoire (second challenge of recipient mice) those that received naïve cells are well protected at a transferred cell number (TCN) of $1 \times 10^5$ cells and not protected by transfer of $10^4$ cells (FIG. 1). In contrast, transfer of $10^2$ cells from actively responding mice conferred immunity to challenge indicating dramatic expansion of the protective T cell repertoire. With cells taken from recovered mice the capacity of cells required to protect the recipient animals is between the number required from naïve or actively responding mice with numbers closer to the naïve animals. This is due to the contraction of responding cell populations and the establishment of a memory pool of cells.

The most interesting of these three groups in terms of antigen identification is the group that received low numbers of cells from actively responding mice. In this experiment, the numbers required to see protection of at least some individuals lies between 100 and 1000 cells. Clearly, each and every donor individual is different and the precise level of protective cells can differ between individuals based upon a variety of stochastic events that naturally occur in the immune response. Nonetheless, the number of between 1000 and 100 cells that can confer protection is dramatically different to the normal number of T cells that exist in a mouse (approx 100 million).

The low number of cells required for protection indicate that it is possible to identify the T cell receptors that are present in "restricted repertoire" of protected versus non-protected animals. It is thus possible to identify the effective T cell receptors which, by definition, recognise the protective antigen(s).

Example 2

Identifying TCR that Associate with Protection

Figure 2:
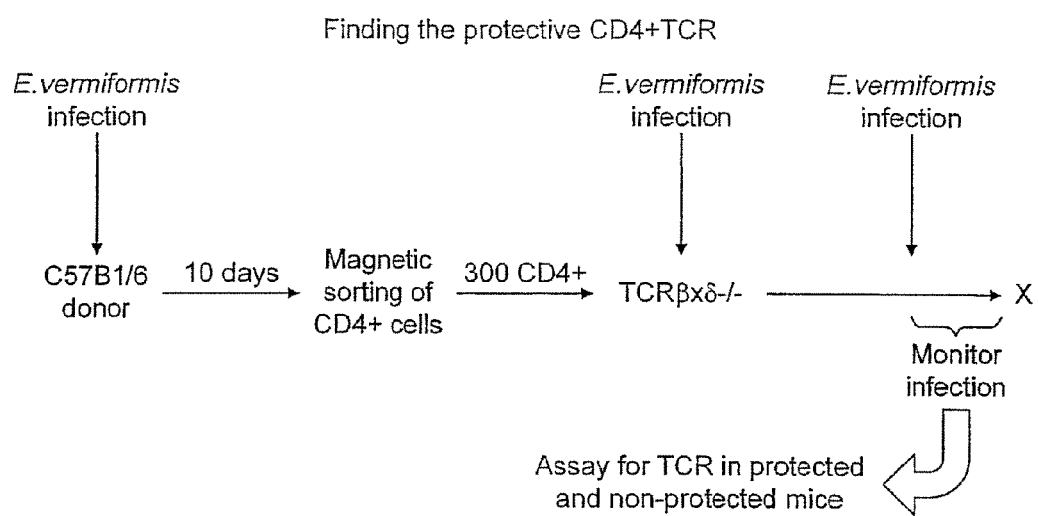
FIG. 2 is a schedule showing a method for finding CD4+ cell specificities and their TCRs
Figure 3:
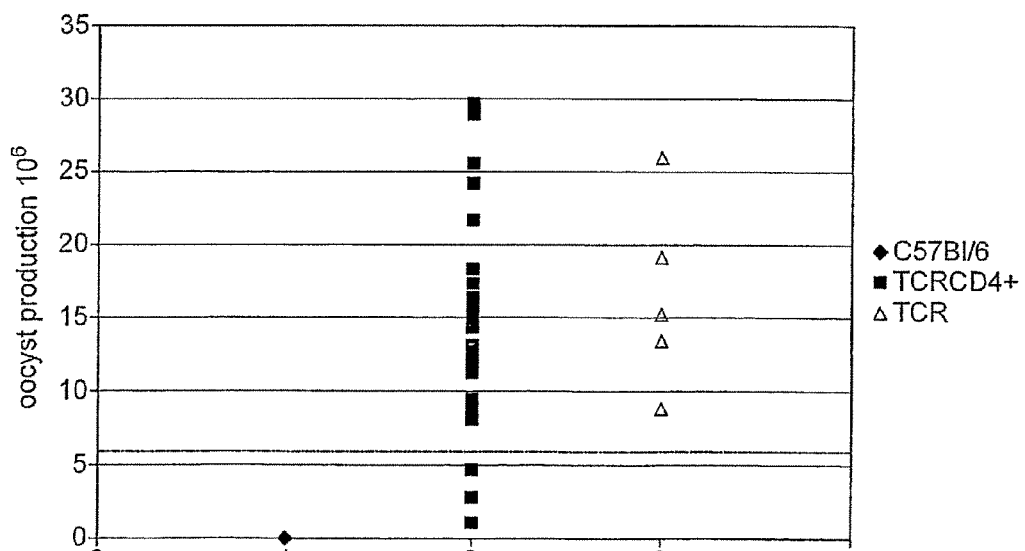
FIG. 3 shows oocyst output from TCR(β×δ)−/− mice which received 300 CD4+ T cells.

CD4+ T cell populations derived from 10 dppi infected C57 BL/6 mice (actively responding) are magnetically sorted and adoptively transferred these into TCR($\beta \times \delta$)-/- recipients at 300-600 T cells/mouse. The schedule is depicted in FIG. 2. In each experiment a single donor C57 BL/6 mouse (female, 6-8 weeks old) is primed by infection with 50 oocysts. The CD4+ T cell fraction is obtained by purification of MLN lymphocytes at 10 dppi and mixing with anti-CD4 conjugated paramagnetic beads (e.g. Miltenyi™) and positive sorting with the AutoMACs system (e.g. Miltenyi™) according to manufacturers' instructions. Recipient animals (TCR[$\beta \times \delta$]-/-) receive 300 sorted cells and are given the first "expansion" infection 7 days post transfer, allowed to recover and given the second "test" infection ~30 dppi. Infections are monitored by production of oocysts in the faeces. In FIG. 3, results of the test infection are presented as oocyst output of individual mice with the dotted line representing the 95% confidence interval for protection. Unmanipulated intact and TCR($\beta \times \delta$)-/- mice are included for reference.

The results demonstrate that of the 30 recipient mice most produced similar numbers of parasites to TCR($\beta \times \delta$)-/- that received no cells (FIG. 3).

Three of the thirty mice in this experiment produce significantly fewer parasites than the other mice and can be considered protected from infection. In four independent experiments approximately 10% of mice that receive low numbers of cells exhibit the protective phenotype (see FIG. 3 for example).

Hence it is possible to generate "protected" TCR repertoires in mice given highly restricted repertoires of T cells and the system may be manipulated to give ~10% protected recipient animals. The capacity to generate ~10% of protected recipients allows comparison of the T cells present in protected and non-protected individuals to identify those TCR causally associated with protective immunity (i.e. those that see protective antigens).

Example 3

Figure 4:
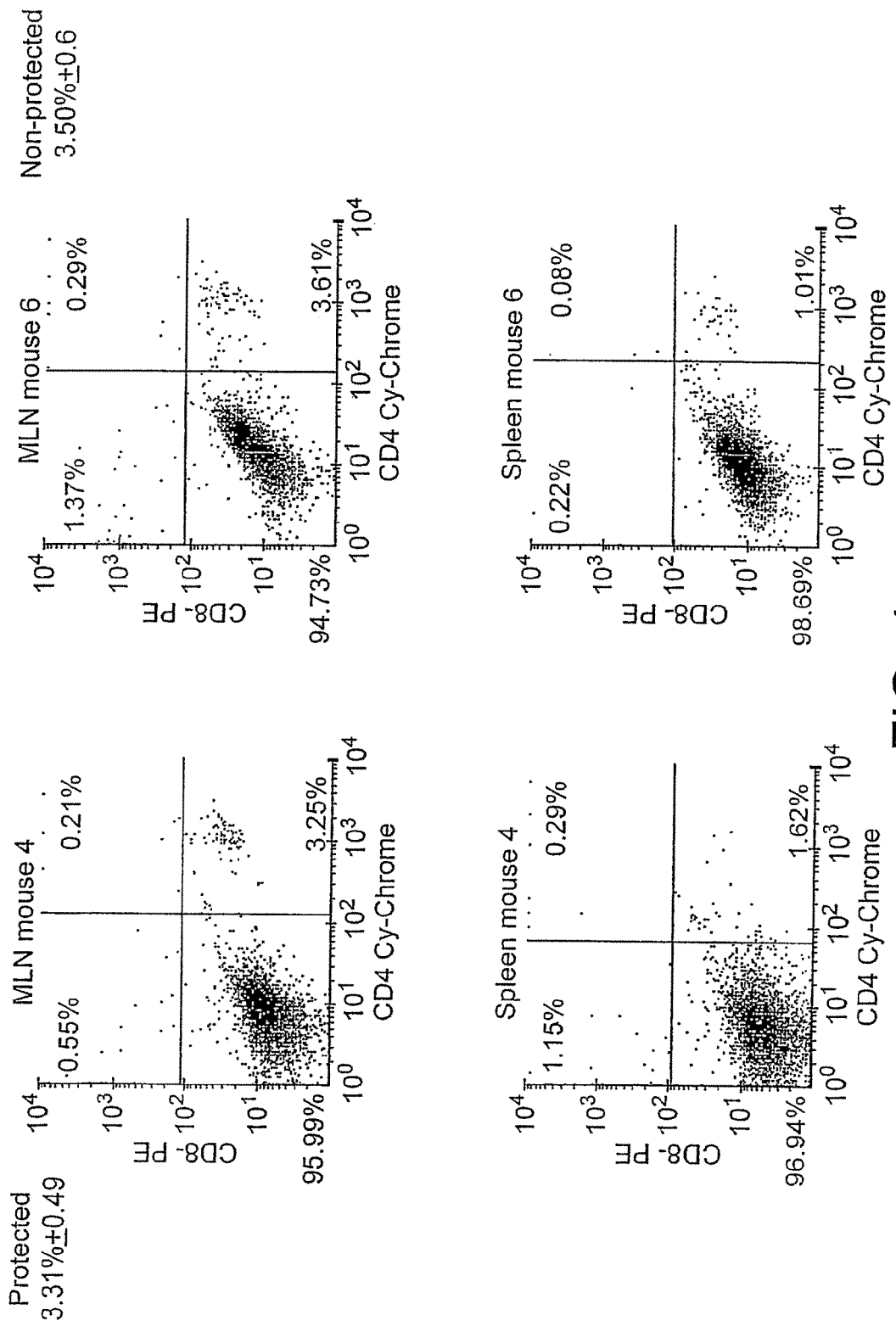
FIG. 4 shows the results of FACS analysis confirming that similar numbers of CD4+ T cells are present in protected and non-protected recipient mice 2 months after transfer with 300 CD4+ T cells.

Similar Numbers of CD4+ T Cells are Present in Protected and Non-Protected "Restricted Repertoire" Recipient Mice A trivial explanation for the results documented in FIG. 3 would be that the transferred CD4+ T cells only survived in the three protected animals. In order to test this, one can examine the CD4+ T cell populations present in all protected and non-protected mice. As indicated in FIG. 4, similar proportions of CD4+ T cells can be detected in all mice irrespective of the "protected" or "non-protected" phenotype displayed by the recipient mice. A population of 1.12±0.09% CD4+ T cells are seen in the spleen of protected animals compared with 1.08±0.11% in the spleen of the twenty-seven non protected animals. Similarly, the percentages of CD4+ T cells seen in the mesenteric lymph nodes (which drain the site of parasite infection) are 3.31±0.49% in protected and 3.50±0.60% in non-protected animals. Hence, the phenotype of the recipient mice in terms of protection against infection cannot be explained by the differential survival or expansion of the adoptively transferred CD4+ T cells.

A conservative estimate of the level of CD4+ T cell expansion (based only upon number of T cells in the spleen and lymph nodes) would be from 300 transferred T cells to a final number of 4 million T cells at the time of analysis. This calculation ignores the fact that many "memory" T cells are located in the tissues, principally the lamina propria and must be considered a substantial underestimate. The final numbers of T cells are as a result of expansion of the transferred cells and although the actual numbers are relatively high these have a maximal repertoire of 300 different TCR. In fact, the actual repertoire is much lower due to the antigen-driven expansions in the donor cell populations that would lead to the donor population having many duplicate TCR expressing cells. A second reason for a "below 300 TCR figure" is that not all transferred cells survive adoptive transfer, resulting in the loss of additional TCR and further restriction of the repertoire in recipient animals.

In a classical T cell proliferation assay with a soluble oocyst antigen preparation from *E. vermiformis* and the spleen cells taken from both "protected" and "non-protected" mice, it is shown that both mice exhibit similar levels of antigen-specific proliferation (data not shown).

Collectively, these data indicate that responding T cells are present in all individuals irrespective of the "protected" or "non-protected" phenotype and supports the premise that much of the response against the infection is irrelevant. Nonetheless, within the response there exists a component of the TCR repertoire that is capable of protection and this can be separated from the responding T cells within a restricted repertoire.

Example 4

Figure 5:
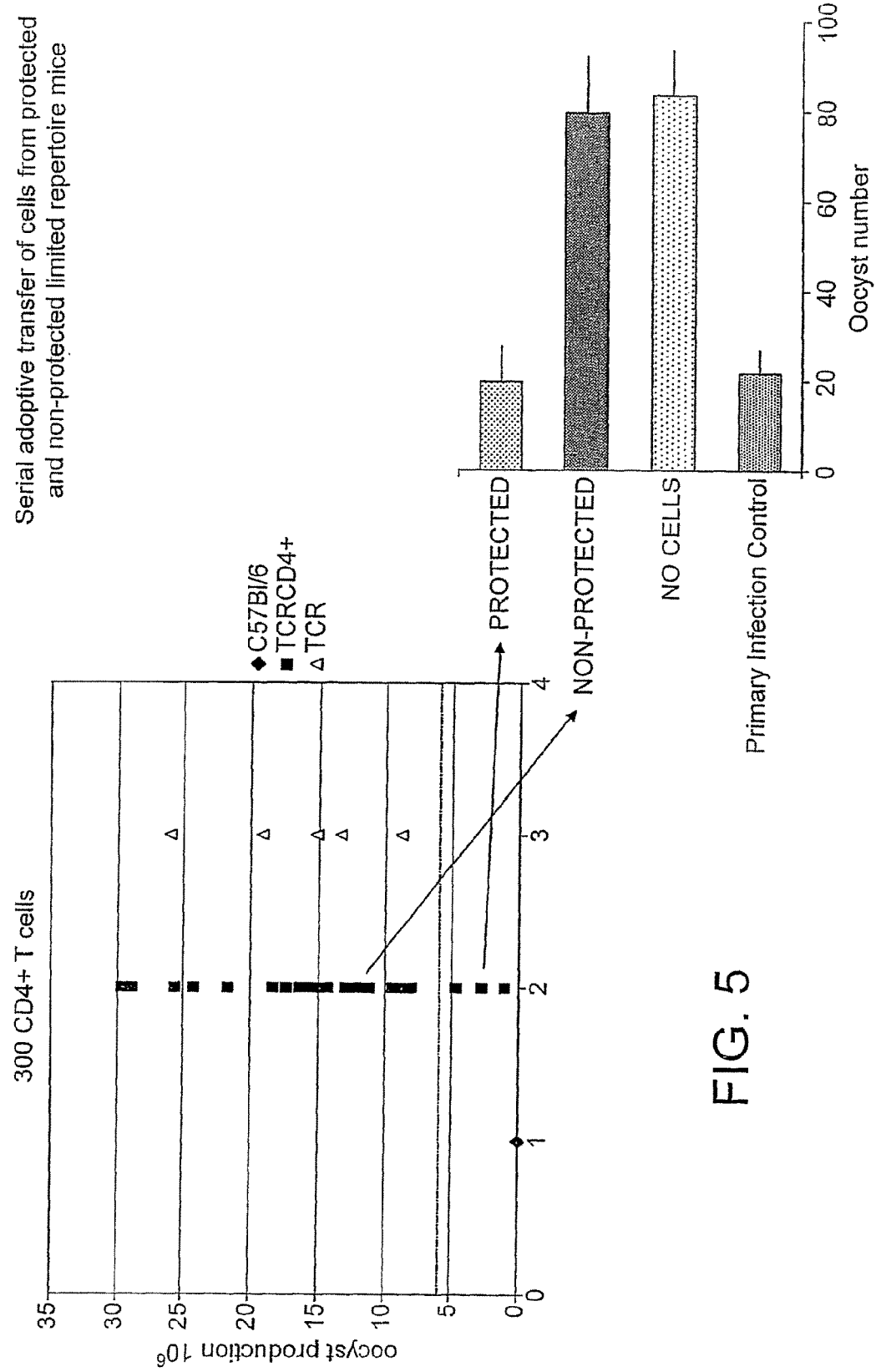
FIG. 5 shows the effect of serial adoptive transfer of a restricted repertoire of cells from protected and non-protected mice to a second group of T-cell deficient recipients

Serial Adoptive Transfer Confirms the Protective Capacity of the Restricted T Cell Populations In order to verify the system, cells are taken from mice previously identified as "protected" or "non-protected" and adoptively transferred into groups of immunodeficient recipients (TCR(β×δ)–/– recipient mice at $10^7$ lymphocytes/mouse). Recipient mice are then challenged with 100 oocysts to test for efficacy of identified T cell populations, magnitude of infection is quantified by oocyst output. This "serial transfer" experiment demonstrates that the cells taken from a "protected" mouse are capable of controlling infection whereas cells taken from an "unprotected" mouse remained unable to control infection as judged by parasite numbers produced in the faeces of the "serial transfer" recipient mice (FIG. 5).

Example 5

Molecular Identification of the TCR Associated with Protection

Figure 6:
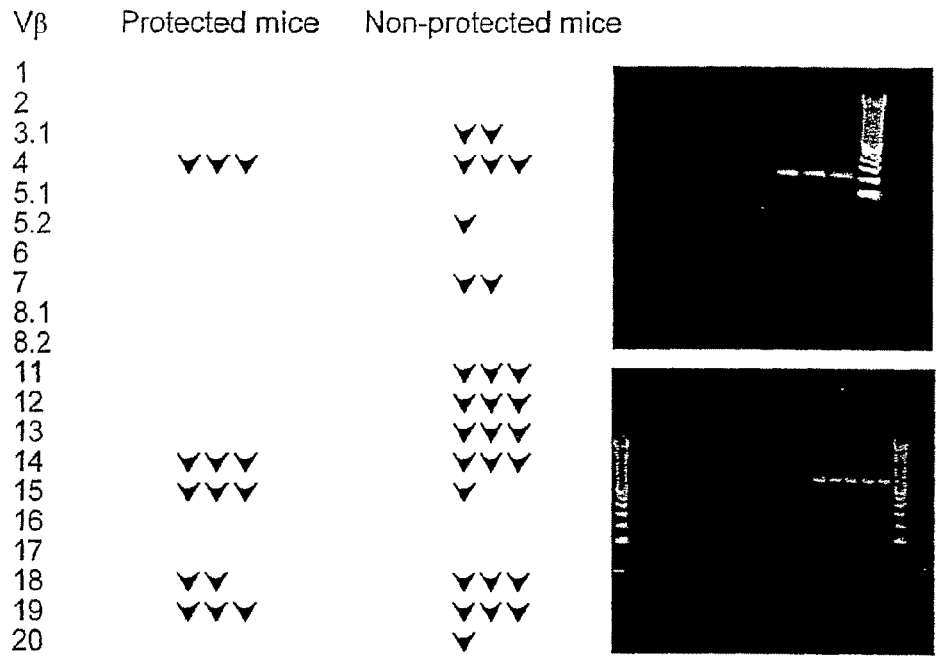
FIG. 6 shows TCRVβ analysis by RT-PCR. A series of RTPCR are undertaken with 3 protected and 3 non-protected mice. Examples of the RTPCR are depicted (right panel) and the results summarised in table format (a symbol representing a positive product from one mouse) with the Vβ annotated on the left-hand side.

In order to assess the identity and complexity of the protective and/or effectiveTCR repertoire (theoretically up to 300 TCR but practically fewer than this number) a simple two-step approach. In the first instance mRNA is extracted from splenocytes (or cells from other organs) taken from "protected" and "non-protected" recipient mice and cDNA prepared using standard techniques. The cDNA is then tested for expression of different TCRVβ families by PCR with primers designed to identify individual TCRVβ families. FIG. 6 shown an example of this method with primers designed to identify TCRVβ4 and TCRVβ14. A full analysis of TCRVβ mRNA expression profiles in the three protected and three selected non-protected mice is presented (FIG. 6).

All three protected mice express mRNA for TCR Vβ4, Vβ14, Vβ15 and Vβ19 which represents a more restricted TCRVβ distribution than seen with the three non-protected mice.

Figure 7:
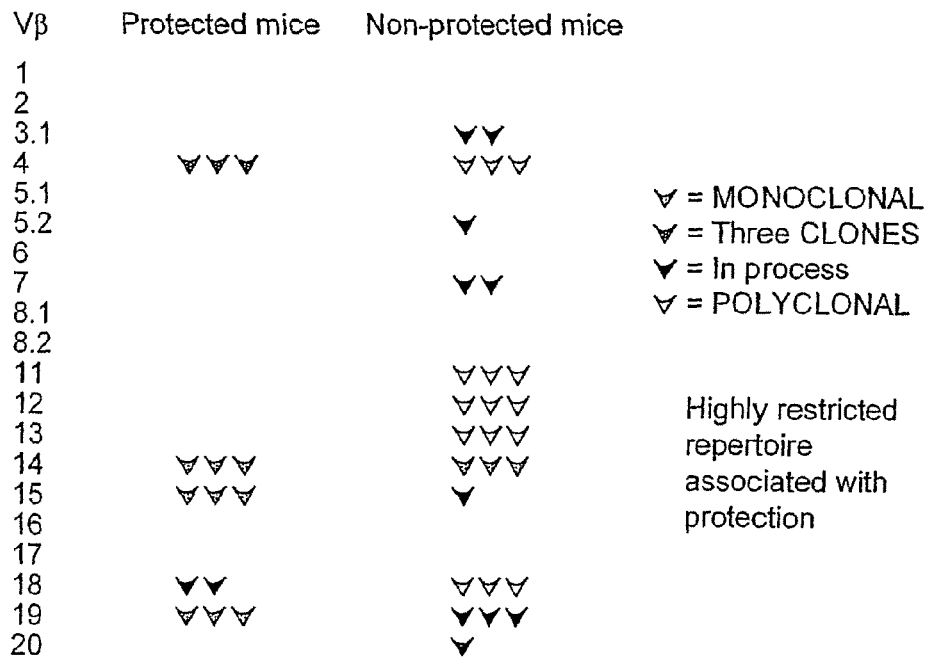
FIG. 7 shows details of the TCR repertoire from each of three protected and three non-protected mice.

Within each TCRVβ many clonal T cell populations will be represented and to identify these clonal populations requires the identification of the sequence that comprises the CDR3 region of the TCR (the region that is hypervariable and responsible for the specificity of antigen recognition). The TCRVβ PCR products are thus cloned into the into plasmids and used to transfect *E. coli*. The inserts derived from at least ten independent "positive" colonies are sequenced. The results from the sequencing of each TCRVβ are summarised in terms of the numbers of different sequences obtained (each representing a clone of T cells; FIG. 7). The number of TCRVβ sequences obtained from "protected" mice are very much fewer in number than those obtained from "non-protected" mice. In total, six TCRVβ sequences are detected in the protected mice and each of these sequences is represented in all three of the protected mice. Three sequences are obtained with TCRVβ4, and only a single sequence is obtained with each of Vβ14, Vβ15 and Vβ19 indicating TCRVβ monoclonality. With "non-protected" mice sequence analysis has been completed with six of the seven TCRVβ represented in all three selected mice and in five of these TCRVβ families the sequences indicated polyclonality (i.e. all of the sequences are different both within and between mice).

Examples of the amino acid sequences encoded by the CDR3 targeting PCR for TCRVβ4 and TCRVβ14 are depicted in FIG. 8 and the frequencies of each sequence is depicted in brackets. Interestingly, within TCRVβ4 where three sequences are obtained with each of the protected mice and none of the non-protected mice the frequencies for each sequence are similar with all three of the protected mice. With TCRVβ 14, a monoclonal CDR3 sequence is obtained with the three protected mice with a CDR3 amino acid sequence of "RRNI". The TCR repertoires that associate with protection in this experiment are quite remarkable in that we can identify six TCRVβ CDR3 sequences that entirely associate with protection. The presence of such a low number of "effective" TCR offers a massive advantage in the search for protective antigens.

References:

1. Barry, M. A., D. P. Howell, H. A. Andersson, J. L. Chen, and R. A. Singh. 2004. Expression library immunization to discover and improve vaccine antigens. Immunol Rev 199: 68-83.
2. Boen, E., A. R. Crownover, M. McIlhaney, A. J. Korman, and J. Bill. 2000. Identification of T cell ligands in a library of peptides covalently attached to HLA-DR4. J Immunol 165:2040-7.
3. Currier, J. R. a. R., M. A. 2000. Spectratype/Immunoscope analysis of the expressed TCR repertoire, p. 10.28.1-10.28.24. In J. E. Coligan, Kruisbeek, A. M., Margulies, D. H., Shevack, E. M., Strober, W. (ed.), Current Protocols in Immunology, vol. 2. Wiley, New York.
4. Fleischer, B., A. Necker, C. Leget, B. Malissen, and F. Romagne. 1996. Reactivity of mouse T-cell hybridomas expressing human Vbeta gene segments with staphylococcal and streptococcal superantigens. Infect Immun 64:987-94.
5. Fox, C. J. a. D., J. S. 1997. Molecular analysis of mouse T cell receptor expression using PCR, p. 10.27.1-10.27.20. In J. E. Coligan, Kruisbeek, A. M., Margulies, D. H., Shevack, E. M., Strober, W. (ed.), Current Protocols in Immunology, vol. 2. Wiley, New York.
6. Gomes, L. I., R. L. Silva, B. S. Stolf, E. B. Cristo, R. Hirata, F. A. Soares, L. F. Reis, E. J. Neves, and A. F. Carvalho. 2003. Comparative analysis of amplified and nonamplified RNA for hybridization in cDNA microarray. Anal Biochem 321:244-51.
7. Goyarts, E. C., Z. Vegh, A. M. Kalergis, H. Honig, N. J. Papadopoulos, A. C. Young, C. T. Thomson, H. C. Chang, S. Joyce, and S. G. Nathenson. 1998. Point mutations in the beta chain CDR3 can alter the T cell receptor recognition pattern on an MHC class I/peptide complex over a broad interface area. Mol Immunol 35:593-607.
8. Hanks, M., W. Wurst, L. Anson-Cartwright, A. B. Auerbach, and A. L. Joyner. 1995. Rescue of the En-1 mutant phenotype by replacement of En-1 with En-2. Science 269:679-82.
9. Hazbon, M. H., and D. Alland. 2004. Hairpin primers for simplified single-nucleotide polymorphism analysis of *Mycobacterium tuberculosis* and other organisms. J Clin Microbiol 42:1236-42.
10. Joyner, A. L. e. a. 1999. Gene targeting: A practical approach. Oxford University Press, Oxford.
11. Kanagawa, O., and R. Maid. 1989. Inhibition of MHC class II-restricted T cell response by Lyt-2 alloantigen. I Exp Med 170:901-12.
12. Klur, S., K. Toy, M. P. Williams, and U. Certa. 2004. Evaluation of procedures for amplification of small-size samples for hybridization on microarrays. Genomics 83:508-17.
13. Kuchroo, V. K., M. C. Byrne, E. Greenfield, M. J. Whitters, E. A. Nalefsky, A. Rao, M. Collins, and M. E. Dorf. 1995. Transfection of TCR alpha-chains into suppressor and T helper cell hybridomas. Production of suppressor factors with predicted antigen specificity. J Immunol 154:5030-8.
14. Letourneur, F., and B. Malissen. 1989. Derivation of a T cell hybridoma variant deprived of functional T cell receptor alpha and beta chain transcripts reveals a nonfunctional alpha-mRNA of BW5147 origin. Eur J Immunol 19:2269-74.
15. Maeji, N. J., A. M. Bray, and H. M. Geysen. 1990. Multipin peptide synthesis strategy for T cell determinant analysis. J Immunol Methods 134:23-33.
16. Pajot, A., M. L. Michel, N. Fazilleau, V. Pancre, C. Auriault, D. M. Ojcius, F. A. Lemonnier, and Y. C. Lone. 2004. A mouse model of human adaptive immune functions: HLA-A2.1-/HLA-DR1-transgenic H-2 class I-/class II-knockout mice. Eur J Immunol 34:3060-9.
17. Sanchez, J. A., K. E. Pierce, J. E. Rice, and L. J. Wangh. 2004. Linear-after-the-exponential (LATE)-PCR: an advanced method of asymmetric PCR and its uses in quantitative real-time analysis. Proc Natl Acad Sci USA 101:1933-8.
18. Schleicher, U., M. Rollinghoff, and A. Gessner. 2000. A stable marker for specific T-cells: a TCR alpha/green fluorescent protein (GFP) fusionprotein reconstitutes a functionally active TCR complex. J Immunol Methods 246:165-74.
19. Shastry, B. S. 1998. Gene disruption in mice: models of development and disease. Mol Cell Biochem 181:163-79.
20. Shibui, A., Y. Ohmori, Y. Suzuki, M. Sasaki, S. Nogami, S. Sugano, and J. Watanabe. 2001. Effects of DNA vaccine in murine malaria using a full-length cDNA library. Res Commun Mol Pathol Pharmacol 109:147-57.
21. Stirewalt, D. L., E. L. Pogosova-Agadjanyan, N. Khalid, D. R. Hare, P. A. Ladne, O, Sala-Torra, L. P. Zhao, and J. P. Radich. 2004. Single-stranded linear amplification protocol results in reproducible and reliable microarray data from nanogram amounts of starting RNA. Genomics 83:321-31.
22. Stone, J. D., W. E. Demkowicz, Jr., and L. J. Stern. 2005. HLA-restricted epitope identification and detection of functional T cell responses by using MHC-peptide and costimulatory microarrays. Proc Natl Acad Sci USA 102:3744-9.
23. Tahara, H., K. Fujio, Y. Araki, K. Setoguchi, Y. Misaki, T. Kitamura, and K. Yamamoto. 2003. Reconstitution of CD8+ T cells by retroviral transfer of the TCR alpha beta-chain genes isolated from a clonally expanded P815-infiltrating lymphocyte. J Immunol 171:2154-60.
24. Tobery, T. W., S. Wang, X. M. Wang, M. P. Neeper, K. U. Jansen, W. L. McClements, and M. J. Caulfield. 2001. A simple and efficient method for the monitoring of antigen-specific T cell responses using peptide pool arrays in a modified ELISpot assay. J Immunol Methods 254:59-66.
25. Vidal, K., C. Daniel, M. Hill, D. R. Littman, and P. M. Allen. 1999. Differential requirements for CD4 in TCR-ligand interactions. J Immunol 163:4811-8.
26. Villarreal-Ramos, B., J. Sanchez-Garcia, N. Stoker, E. Timms, D. Chomer, K. Raff, and N. A. Mitchison. 1991. Screening gene expression libraries for epitopes recognized in *Mycobacterium leprae* by mouse T cells. Eur J Immol 21:2621-4.
27. Warren, R. L., D. Lu, D. R. Sizemore, L. S. Baron, and D. J. Kopecko. 1990. Method for identifying microbial antigens that stimulate specific lymphocyte responses: application to *Salmonella*. Proc Natl Acad Sci USA 87:9823-7.
28. Xiang, Z. Q., and H. C. Ertl. 1994. A simple method to test the ability of individual viral proteins to induce immune responses. J Virol Methods 47:103-16.
29. Yoshida, R., T. Yoshioka, S. Yamane, T. Matsutani, T. Toyosaki-Maeda, Y. Tsuruta, and R. Suzuki. 2000. A new method for quantitative analysis of the mouse T-cell receptor V region repertoires: comparison of repertoires among strains. Immunogenetics 52:35-45.
30. Zumla, A., A. McCormack, A. George, R. Batchelor, and R. Lechler. 1992. Use of a murine T-cell hybridoma expressing human T-cell receptor alpha- and beta-gene products as a tool for the production of human T-cell receptor-specific monoclonal antibodies. Hum Immunol 35:141-8.
31. Rose, M. E., D. G. Owen, and P. Hesketh. 1984. Parasitology 88 (Pt 1):45-54.)

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular studies using flow cytometry or related fields are intended to be within the scope of the following claims.

The invention claimed is:

1. A method for identifying a T-cell receptor (TCR) protective against a disease, which comprises the following steps:
   i) obtaining T cells from a donor non-human animal which comprises T cells protective against the disease amongst its complete T cell repertoire;
   ii) adoptive transfer of the T cells into a plurality of T-cell deficient recipient non-human animals in a number such that, following subsequent disease challenge, at least one recipient animal is protected against the disease but at least one animal remains un-protected;
   iii) analyzing TCRVβ sequences of TCR(s) present in the at least one protected and the at least one unprotected animals; and
   iv) identifying a TCR protective against the disease by identifying TCRVβ sequence(s) present in the at least one protected animal and not present in the at least one unprotected animal.

2. A method according to claim 1 wherein the donor animal is an immunologically responding non-human animal.

3. A method according to claim 1, wherein the number of cells appropriate for use in step ii is determined by performing a limiting dilution analysis.

4. A method according to claim 1, wherein the number of T cells transferred to each recipient animal is such that less than half of the recipient animals are protected against the disease.

5. A method according to claim 4, wherein the number of T cells transferred to each recipient animal is such that less than 10% of the recipient animals are protected against the disease.

6. A method according to claim 1, wherein fewer than 1000 T cells are transferred to each recipient animal.

7. A method according to claim 1, wherein the T cells collected from the donor animal are sorted to increase the proportion of CD4+ or CD8+ cells prior to adoptive transfer.

8. A method according to claim 1, wherein T cells from a protected recipient animal are sorted into CD4+ or CD8+ cell subsets prior to analyzing the TCRVβ sequences.

9. A method according to claim 1, wherein the donor and recipient non-human animals are transgenic for human MHC.

10. A method for screening for an antigen or antigenic determinant which is capable of inducing a protective immune response, which comprises the following steps:
    (i) identifying a protective TCR by the method according to claim 1;
    (ii) producing a cell expressing the protective TCR;
    (iii) using the TCR-expressing cell to screen candidate antigens/antigenic determinants; and
    (iv) selecting an antigen/antigenic determinant recognised by the protective/effective TCR.

11. A method according to claim 1, which also comprises the step:
    (v) identifying the TCRVα chain(s) which correspond(s) to the identified TCRVβ sequence(s).

12. A method for identifying a T-cell receptor (TCR) protective against a disease comprising the following steps:
    i) obtaining T cells from a donor non-human animal which comprises T cells protective against the disease amongst its complete T cell repertoire;
    ii) adoptive transfer of a restricted repertoire of the T cells into a plurality of T-cell deficient recipient non-human animals in a number such that, following subsequent disease challenge, at least one recipient animal is protected against the disease but at least one animal remains un-protected;
    iii) analyzing TCRVβ sequences of TCR(s) present in the protected and unprotected animals; and iv) identifying a TCR protective against the disease by identifying TCRVβ sequence(s) present in the at least one protected animal and not present in the at least one unprotected animal.

13. The method of claim 12, wherein the restricted repertoire of T cells comprises 100 to 1000 T cells.

* * * * *

UNITED STATES PATENT AND TRADEMARK OFFICE
CERTIFICATE OF CORRECTION

PATENT NO. : 8,404,454 B2
APPLICATION NO. : 12/745862
DATED : March 26, 2013
INVENTOR(S) : Adrian Smith Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 268 days.

Signed and Sealed this

First Day of September, 2015

Michelle K. Lee
*Director of the United States Patent and Trademark Office*